US00PP30299P3

(12) United States Plant Patent

Klemm et al.

(10) Patent No.: US PP30,299 P3
(45) Date of Patent: Mar. 19, 2019

(54) *DIANTHUS* PLANT NAMED 'KLEDP16188'

(50) Latin Name: *Dianthus caryophyllus*
Varietal Denomination: KLEDP16188

(71) Applicant: Klemm+Sohn GmbH & Co. KG, Stuttgart (DE)

(72) Inventors: Nils Klemm, Stuttgart (DE); Lena Gutbrodt, Bempflingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 30 days.

(21) Appl. No.: 15/731,278

(22) Filed: May 17, 2017

(65) Prior Publication Data

US 2018/0338401 P1 Nov. 22, 2018

(51) Int. Cl.
*A01H 5/02* (2018.01)
*A01H 6/30* (2018.01)

(52) U.S. Cl.
USPC ..... Plt./273
CPC ..... *A01H 6/305* (2018.05)

(58) Field of Classification Search
USPC ..... Plt./263.1, 272, 273
See application file for complete search history.

*Primary Examiner* — Susan McCormick Ewoldt
*Assistant Examiner* — Karen M Redden
(74) *Attorney, Agent, or Firm* — Barbara Campbell; Cochran Freund & Young LLC

(57) ABSTRACT

A new *Dianthus* plant particularly distinguished by light-purple double flowers with dark-red purple blotches around the center and an upright habit, is disclosed.

1 Drawing Sheet

Genus and species: *Dianthus caryophyllus*.
Variety denomination: 'KLEDP16188'.

BACKGROUND OF THE NEW PLANT

The present invention comprises a new and distinct variety of *Dianthus*, botanically known as *Dianthus caryophyllus*, and hereinafter referred to by the variety name 'KLEDP16188'. 'KLEDP16188' originated from a cross between the proprietary female *Dianthus* parent 'DCP-2010-0039' (unpatented) and the proprietary male *Dianthus* parent 'DCP-2010-0044' (unpatented) in May 2011 in Stuttgart, Germany in a plastic greenhouse. A single plant was selected in June 2012 in Stuttgart, Germany.

In August 2012, 'KLEDP16188' was first vegetatively propagated by vegetative cuttings. 'KLEDP16188' was found to reproduce true to type in successive generations of asexual propagation in Stuttgart, Germany via vegetative cuttings.

SUMMARY

The following are the most outstanding and distinguishing characteristics of this new variety when grown under normal horticultural practices in Stuttgart, Germany.

1. Light-purple double flowers with dark-red purple blotches around the center; and
2. An upright habit.

DESCRIPTION OF THE PHOTOGRAPH

This new *Dianthus* plant is illustrated by the accompanying photograph of a plant approximately 8-weeks old and grown in a greenhouse in Stuttgart, Germany. The photograph shows the whole plant, including the flowers and foliage and buds and was taken in August 2012 in Stuttgart, Germany. The colors shown are as true as can be reasonably obtained by conventional photographic procedures.

DESCRIPTION OF THE NEW VARIETY

The following detailed descriptions set forth the distinctive characteristics of 'KLEDP16188'. The data which define these characteristics were collected from asexual reproductions carried out in Stuttgart, Germany. Data was collected in April 2013 on 7-month old plants grown in a plastic greenhouse. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus caryophyllus*.
- *Common*.—Pot carnation.
- *Designation*.—'KLEDP16188'.

Parentage:
- *Female parent*.—The proprietary *Dianthus* parent 'DCP-2010-0039' (unpatented).
- *Male parent*.—The proprietary *Dianthus* parent 'DCP-2010-0044' (unpatented).

Plant:
- *Plant form*.—Upright, potted plant.
- *Plant height*.—13.0 cm to 15.0 cm.
- *Plant diameter or spread*.—16.0 cm to 18.0 cm.
- *Propagation type*.—Vegetative cuttings, stem cuttings.
- *Time to produce a rooted young plant*.—14 to 16 days.
- *Root description*.—White, fine.
- *Rooting habit (shape)*.—Lanceolate.

Lateral branches:
- *Length*.—10.0 cm to 12.0 cm.
- *Diameter*.—0.3 cm to 0.5 cm.
- *Internode length*.—2.0 cm to 3.0 cm.
- *Number of internodes per branch/stem*.—3 to 5.

*Node length.*—0.2 cm to 0.4 cm.
*Node diameter.*—0.2 cm to 0.3 cm.
*Texture.*—Smooth.
*Color.*—RHS 143C.
*Branch/stem appearance.*—Solid.

Foliage:
*Arrangement.*—Opposite.
*Length.*—4.0 cm to 6.0 cm.
*Width.*—0.5 cm to 0.7 cm.
*Shape.*—Lanceolate.
*Apex.*—Acute.
*Base.*—Obtuse.
*Margin.*—Entire.
*Texture (both upper and lower surfaces).*—Smooth.
*Immature leaf color.*—Upper surface: RHS 137A. Lower surface: RHS 137C.
*Mature leaf color.*—Upper surface: RHS N137A. Lower surface: RHS N137D.
*Venation pattern.*—Palmate.
*Venation color.*—Upper surface: RHS N137A. Lower surface: RHS N137D.

Flowers:
*Flower type and habit.*—Round, double, small sprays.
*Fragrance.*—Present.
*Natural flowering season.*—Spring to fall.
*Position of flowers relative to the foliage.*—Slightly above.
*Number of flowers per spray.*—2 to 3.
*Flower longevity on the plant.*—10 to 14 days.
*Buds.*—Length: 1.5 cm to 1.8. Diameter: 0.8 cm to 1.0 cm. Shape: Elliptic. Color: RHS N144D and RHS 137B. Extrusion of the styles at the bud stage: Absent.
*Corolla.*—Quantity of petals and arrangement: 17 to 20. Corolla height: 1.5 cm to 2.0 cm. Petal length: 3.0 cm. Petal width: 1.5 cm to 1.8 cm. Petal shape: Spoon-shaped. Petal apex: Obtuse. Petal base: Acute. Petal margin: Crenate. Depth of petal margin: Medium. Petal texture (both upper and lower surfaces): Smooth. Petal color: Immature: Upper surface: RHS N74A and RHS 59A. Lower surface: RHS 75A. Mature: Upper surface: RHS 77C and RHS 61A. Lower surface: RHS 69C.
*Calyx.*—Quantity of sepals and arrangement: Composed of 5 sepals. Shape: Campanulate. Calyx height: 2.0 cm to 2.2 cm. Calyx diameter (at the apex): 0.6 cm to 0.8 cm. Sepal texture (both upper and lower surfaces): Smooth. Sepal color: Upper surface: RHS 137A. Lower surface: RHS 137D.

Peduncles:
*Length.*—10.0 cm to 12.0 cm.
*Diameter.*—0.2 cm.
*Strength.*—Moderate.
*Texture.*—Smooth.
*Color.*—RHS 137A.

Reproductive organs:
*Stamens.*—Quantity per flower: Moderate. Filament length: 0.4 cm to 0.6 cm. Filament color: RHS NN155B. Anther length: 0.1 cm. Anther diameter: 0.05 cm. Anther color: RHS 18B. Pollen amount: Sparse.
*Pistils.*—Quantity per flower: 1. Pistil length: 0.1 cm. Style length: 1.5 cm to 1.7 cm. Style color: RHS NN155B. Stigma shape: Filamentous. Stigma color: RHS 70B. Ovary size: 0.6 cm to 0.8 cm. Ovary shape: Oval. Ovary color: RHS 144B and RHS N144D.

Fruit and seed set: Seed is sometimes observed, but no information on the seed is available.

Disease and pest/insect resistance: No disease and pest/insect resistance observed.

COMPARISON WITH PARENTAL LINES AND KNOWN VARIETY

'KLEDP16188' is distinguished from the mutation parent as described in Table 1.

TABLE 1

Comparison with Parental Lines

| Characteristic | 'KLEDP16188' | Female Parent 'DCP-2010-0039' | Male Parent 'DCP-2010-0044' |
|---|---|---|---|
| Leaf sensitivity to low iron concentration | Not sensitive | Sensitive | Sensitive |

'KLEDP16188' can be compared to the commercial *Dianthus* variety 'KLEDP13122' (U.S. Plant Pat. No. 26,738). Differences between the varieties are described in Table 2.

TABLE 2

Comparison with Similar Variety

| Characteristic | 'KLEDP16188' | 'KLEDP13122' |
|---|---|---|
| Plant and growth habit | Round, upright | Upright |
| Internode length | 2.0 cm to 3.0 cm | 1.5 cm |

We claim:

1. A new and distinct variety of *Dianthus* plant designated 'KLEDP16188' as shown and described herein.

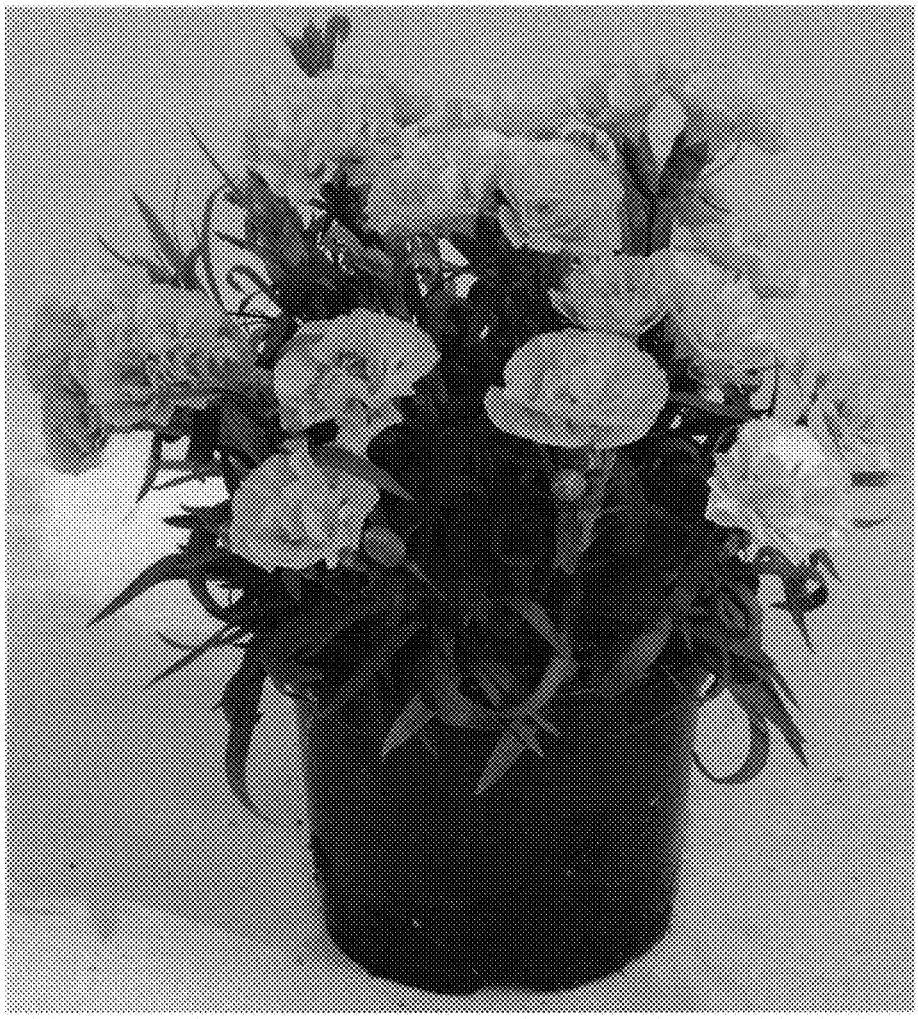

* * * * *